US009517996B2

(12) United States Patent
Laplaza et al.

(10) Patent No.: US 9,517,996 B2
(45) Date of Patent: Dec. 13, 2016

(54) PURIFICATION OF POLYCARBOXYLIC ACIDS

(71) Applicant: Verdezyne, Inc., Carlsbad, CA (US)

(72) Inventors: Jose Laplaza, Fallbrook, CA (US); William Andrew Evanko, Golden, CO (US); Jason H. Radany, Murrieta, CA (US)

(73) Assignee: Verdezyne, Inc., Carlsbad, CA (US)

( * ) Notice: Subject to any disclaimer, the term of this patent is extended or adjusted under 35 U.S.C. 154(b) by 0 days.

(21) Appl. No.: 14/738,600

(22) Filed: Jun. 12, 2015

(65) Prior Publication Data

US 2015/0361024 A1 Dec. 17, 2015

Related U.S. Application Data

(60) Provisional application No. 62/011,500, filed on Jun. 12, 2014.

(51) Int. Cl.
| | | |
|---|---|---|
| *C07C 51/43* | (2006.01) | |
| *C07C 55/02* | (2006.01) | |
| *C07C 55/20* | (2006.01) | |
| *C07C 51/42* | (2006.01) | |
| *C07C 51/47* | (2006.01) | |

(52) U.S. Cl.
CPC ............... *C07C 51/43* (2013.01); *C07C 51/42* (2013.01); *C07C 51/47* (2013.01); *C07C 55/02* (2013.01); *C07C 55/20* (2013.01)

(58) Field of Classification Search
CPC .......... C07C 51/43; C07C 51/42; C07C 51/47; C07C 55/02; C07C 55/20
See application file for complete search history.

(56) References Cited

U.S. PATENT DOCUMENTS

| | | | |
|---|---|---|---|
| 2,847,467 A | 8/1958 | Steadman et al. | |
| 2,960,533 A | 11/1960 | Frank et al. | |
| 4,149,013 A * | 4/1979 | Klein | C07C 51/487 562/593 |
| 5,068,419 A * | 11/1991 | Kulprathipanja | C07C 51/47 562/580 |
| 2009/0054610 A1 | 2/2009 | Gross et al. | |

FOREIGN PATENT DOCUMENTS

| | | |
|---|---|---|
| CN | 104693018 A | 6/2015 |
| WO | WO-2014100461 A2 | 6/2014 |

OTHER PUBLICATIONS

"International search report and written opinion dated Sep. 16, 2015 for PCT Application No. US2015/035634."

* cited by examiner

*Primary Examiner* — Shailendra Kumar
(74) *Attorney, Agent, or Firm* — Wilson Sonsini Goodrich & Rosati

(57) ABSTRACT

A process for purifying a polycarboxylic acid from a mixture is provided. Optionally, the mixture is an aqueous solution and optionally the process comprises an acidification step and/or the use of one or more organic solvents. Also provided in part are compositions of polycarboxylic acids.

15 Claims, No Drawings

PURIFICATION OF POLYCARBOXYLIC ACIDS

CROSS-REFERENCE TO RELATED APPLICATION

This application claims the benefit of U.S. Provisional Application No. 62/011,500, filed Jun. 12, 2014, which application is incorporated herein by reference in its entirety.

FIELD OF THE INVENTION

The technology relates in part to purification of a polycarboxylic acid of interest from a mixture of organic materials or molecules.

BACKGROUND OF THE INVENTION

Polycarboxylic acids have many uses as chemical intermediates or monomers for industrial production of nylons, plastics, and many other industrial polymers. At present, the vast majority of polycarboxylic acid monomers are produced from petroleum. Recently, it has become possible to utilize genetically engineered microorganisms to produce polycarboxylic acids at an industrial scale using carbon sources other than petroleum such as various sugars, fats and oils. The engineered microorganisms can be cultured in a suitable liquid medium containing a carbon source or sources as well as other required nutrients. When cultured under desirable temperature, pH, dissolved oxygen and the like, the microorganisms can produce and secrete the polycarboxylic acids into the culture medium. The polycarboxylic acids can then be separated from this medium and purified to the extent necessary for use in particular industrial processes.

SUMMARY OF THE INVENTION

Provided in certain aspects are methods for purifying a polycarboxylic acid of interest from an aqueous mixture, comprising: (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; and (d) collecting the purified polycarboxylic acid. In certain embodiments, the polycarboxylic acid of interest is at least one of octanedioic acid, nonanedioic acid, decanedioic acid, Brassilic acid (undecanedioic acid or UDDA), dodecanedioic acid (DDDA), tetradecanedioic acid (TDDA) and the like. Also provided are methods for purifying a polycarboxylic acid of interest from an aqueous mixture, comprising: (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; (d) collecting the purified polycarboxylic acid; and optionally a separation step between (a) and (b) to separate the precipitated polycarboxylic acid. In some methods described herein, the aqueous solution may be a fermentation broth. In certain methods, the polycarboxylic acid of interest is a dicarboxylic acid.

Provided herein are methods described herein for purifying a polycarboxylic acid of interest comprising culturing a microorganism to produces the polycarboxylic acid of interest in an aqueous medium (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; and (d) collecting the purified polycarboxylic acid. In certain aspects, the aqueous medium may be a fermentation broth. In certain aspects, the fermentation broth comprises at least one feedstock which is a non-petroleum based carbon source. In some aspects, the polycarboxylic acid is obtained without any use of a petroleum based feed stock.

In certain aspects are methods for purifying a polycarboxylic acid of interest from an aqueous mixture as described herein, wherein the polycarboxylic acid is chosen from azelaic acid, sebacic acid, UDDA, DDDA, brassylic acid, TDDA, thapsic acid, traumatic acid, octadecanedioic acid, 9-octadecenedioic acid, octadeca-c6,c9-diene-1,18-dioate octadeca-c3,c6,c9-triene-1,18-dioate, and icosanedioic acid. In certain cases, the polycarboxylic acid is DDDA.

In certain aspects are methods described herein for purifying a polycarboxylic acid of interest from an aqueous mixture as described herein, comprising contacting the polycarboxylic acid with at least one suitable organic solvent. In certain embodiments, the at least one organic solvent is an acid. In some embodiments, the at least one organic solvent is acetic acid. In some cases, the at least one organic solvent is one or more of acetic acid, formic acid, n-Butanol, sec-butanol, isobutanol, tert-butanol, pentanol, hexanol, septanol, octanol, butanone, pentanone, acetone and ethyl acetate. The organic solvent maybe heated to solubilize the polycarboxylic acid of interest. In some cases, the organic solvent(s) is heated 1, 2, 3, 4, 5, 6, 7, 8, 9, or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or greater than 70 degrees above the temperature of the medium comprising the polycarboxylic acid of interest to which the organic solvent is to be added. In some cases, the organic solvent maybe cooled after heating. In some cases the solvent is cooled slowly. In some cases, the organic solvent maybe cooled after heating resulting in precipitating the polycarboxylic acid of interest. The organic solvent maybe heated to about 70 degrees Celsius and then cooled to about 25 degrees Celsius. In some cases, the organic solvent maybe cooled slowly. In some cases the solvent maybe cooled to room temperature at a rate of between 1, 2, 3, 4, 5, 6, 7, 8, 9, 10, 11, 12, 13, 14, or 15 degrees Celcius 180 C per hour, or less than 1 degree Celcius per hour.

In some cases are methods described herein for purifying a polycarboxylic acid of interest from an aqueous mixture as described herein, comprising contacting the polycarboxylic acid with at least one suitable organic solvent, wherein the polycarboxylic acid is one of zelaic acid, sebacic acid, UDDA, DDDA, brassylic acid, TDDA, thapsic acid, traumatic acid, octadecanedioic acid, 9-octadecenedioic acid, octadeca-c6,c9-diene-1,18-dioate octadeca-c3,c6,c9-triene-1,18-dioate, and icosanedioic acid, the at least one organic solvent is acetic acid, which is optionally heated to about 70 degrees Celsius and then optionally cooled to between about 35 and about 20 degrees Celsius. In some cases, the at least one organic solvent is cooled to about 25 degrees Celsius.

In certain aspects are methods described herein for purifying a polycarboxylic acid of interest from an aqueous mixture as described herein, said methods further comprising one or more separating steps. In some cases, a separation step maybe introduced to separate the polycarboxylic acid from an aqueous medium after the polycarboxylic acid is precipitated from said medium by reducing the pH of the aqueous medium comprising the polycarboxylic acid.

In certain aspects are methods described herein for purifying a polycarboxylic acid of interest from an aqueous mixture as described herein, wherein the polycarboxylic acid is at least 5 percent more pure on a weight to weight basis as compared to said aqueous mixture.

In some aspects are compositions of at least one substantially pure polycarboxylic acid, wherein said substantially pure polycarboxylic acid is purified by a method described herein. In an aspect is a composition comprising a substantially pure polycarboxylic acid, wherein said polycarboxylic acid is purified from an aqueous mixture by a method comprising: (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; and (d) collecting the purified polycarboxylic acid. In some cases the substantially pure polycarboxylic acid maybe at least 5, 10, 15, 20, 25, 30, 35, 40, 45, 50, 55, 60, 65, 70, 75, 80, 85, 90, or 95 percent more pure on a weight to weight basis as compared to a corresponding amount of unpurified polycarboxylic acid in the aqueous mixture from which said polycarboxylic acid is purified. In some cases, the substantially pure polycarboxylic acid maybe at least one of azelaic acid, sebacic acid, UDDA, DDDA, brassylic acid, TDDA, thapsic acid, traumatic acid, octadecanedioic acid, 9-octadecenedioic acid, octadeca-c6,c9-diene-1,18-dioate octadeca-c3,c6,c9-triene-1,18-dioate, and icosanedioic acid.

In some embodiments are provided methods for purifying a polycarboxylic acid of interest from an aqueous mixture as described herein, wherein the method does not include a nanofiltration step. In some cases, the method may include a nanofiltration step. In some cases, the method may not include crystallization of the polycarboxylic acid. In some cases, the aqueous solution may be a fermentation broth.

Provided herein is any method described above or below for purifying a polycarboxylic acid of interest from an aqueous mixture, comprising: (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; and (d) collecting the purified polycarboxylic acid.

In some embodiments is any method described above or below, comprising a separating process between (a) reducing the pH of the aqueous medium comprising the polycarboxylic acid such that the polycarboxylic acid is precipitated from said medium; and (b) contacting the precipitated polycarboxylic acid with at least one suitable organic solvent at one or more selected temperatures.

In some embodiments is any method described above or below, wherein the aqueous solution is a fermentation broth.

In some embodiments is any method described above or below, wherein the polycarboxylic acid of interest is a dicarboxylic acid.

In some embodiments is any method described above or below, wherein the polycarboxylic acid is chosen from azelaic acid, sebacic acid, UDDA, DDDA, brassylic acid, TDDA, thapsic acid, traumatic acid, octadecanedioic acid, 9-octadecenedioic acid, octadeca-c6,c9-diene-1,18-dioate octadeca-c3,c6,c9-triene-1,18-dioate, and icosanedioic acid.

In some embodiments is any method described above or below wherein the polycarboxylic acid is DDDA.

In some embodiments is any method described above or below, wherein the at least one organic solvent is an acid.

In some embodiments is any method described above or below wherein the at least one organic solvent is acetic acid.

In some embodiments is any method described above or below wherein the at least one organic solvent is heated to solubilize the polycarboxylic acid of interest.

In some embodiments is any method described above or below wherein the organic solvent is slowly cooled after heating thereby precipitating the polycarboxylic acid of interest.

In some embodiments is any method described above or below, wherein the polycarboxylic acid is DDDA, the organic solvent is acetic acid is heated to about 70 degrees Celsius and then cooled to about 25 degrees Celsius.

In some embodiments is any method described above or below, further comprising one or more separating steps.

In some embodiments is any method described above or below, wherein the polycarboxylic acid is at least 5 percent more pure on a weight to weight basis as compared with the starting mixture.

In some embodiments is a composition comprising a polycarboxylic acid of interest, wherein the polycarboxylic acid of interest is made according to any method described above or below. In some embodiments is a composition wherein the polycarboxylic acid of interest is DDDA.

Certain non-limiting aspects and embodiments are described further in the following description, examples, and claims.

DETAILED DESCRIPTION OF THE INVENTION

Provided herein are methods for purifying a polycarboxylic acid of interest from a mixture of molecules. In certain embodiments, the polycarboxylic acid of interest can be produced by culturing a microorganism that produces the polycarboxylic acid of interest in an aqueous medium such as a fermentation broth in the presence of at least one non-petroleum carbon source. The polycarboxylic acid of interest can be purified by reducing the pH of the aqueous medium, exposing the polycarboxylic acid of interest to at least one suitable organic solvent, and optionally altering the temperature of the mixture of the at least one suitable organic solvent and polycarboxylic acid of interest. In some embodiments, additional processing steps such as centrifugation or filtration can be selectively employed to further purify the polycarboxylic acid of interest.

The terms "polycarboxylic acid of interest" and "target polycarboxylic acid" as used herein refer to a polycarboxylic acid to be purified or isolated from a mixture of organic molecules and/or from other organic material such as cell mass. Polycarboxylic acids of interest herein have at least eight carbons and have at least two, and optionally more, carboxyl groups. The polycarboxylic acid of interest can be in the form of a partial polycarboxylate species, wherein one or more of the carboxyl groups is not protonated but is in the salt form, while other carboxyl groups are in the acid form; the salt form may include a sodium cation, a potassium cation, a combination thereof or any other cation(s) or positively charged species. Also included herein are a polycarboxylic acid of interest in the fully protonated (acid) form and a polycarboxylic acid of interest in the full salt form. A "polycarboxylic acid of interest" included herein is soluble in water at or below a concentration of 1 gram per liter at 25 degrees Celsius, and is soluble in a mixture of water and an organic solvent (where the organic solvent is miscible with water) at seventy degrees Celsius at a concentration of at least ten grams per liter. In certain embodiments, the polycarboxylic acid of interest is at least eight carbons in length and may optionally be up to 24 or more carbons in length, wherein the total number of carbons in the polycarboxylic acid can be an odd number (9, 11, 13, 15, 17, 19, 21, 23, 25 and the like) or an even number (8, 10, 12, 14, 16, 18, 20, 22, 24, 26 and the like). The carboxyl groups of a polycarboxylic acid of the present invention may be located on any carbon on the molecule, as for example on the terminal carbons of the molecule (the "alpha" or "omega" positions), on one terminal carbon and one or more subterminal (branched) carbon(s) such as in the 1 and 2 positions (i.e., a 1, 2, dicarboxylic acid or an "alpha beta" dicarboxylic acid), or on subterminal (branched or "internal") carbons only. Non limiting examples of polycarboxylic acids included herein are dicarboxylic acids such as 1,8-octanedioic acid ("suberic acid"), 1,10-decanedioic acid ("sebacic acid"), 1,12-dodecanedioic acid ("DDDA" and "lauric diacid"), 1,14-tetradecanedioic acid ("TDDA" and "myristic acid"), 1,16-hexadecanedioic acid ("palmitic acid"), 1,18 octadecanedioic acid ("stearic acid"), eicosanoic diacid, oleic diacid, azeleaic acid, brassylic acid, undecanedioic diacid, palmitoleic diacid, linoleic diacid, linolenic diacid, and pimelic acid. Optionally, a polycarboxylic acid of the present invention may be saturated or unsaturated, and if unsaturated, may have one, two three, four or more double bonds.

The term "mixture" or "mixtures" as used herein refers to two or more different organic molecules and/or organic materials in contact with each other in an aqueous environment, wherein at least one of the compounds or materials is a polycarboxylic acid of interest. In some embodiments, a mixture may contain two or more different polycarboxylic acids, one of which is a polycarboxylic acid of interest. In some embodiments, organic molecules other than a polycarboxylic acid such as, for example, one or more monocarboxylic acid(s), one or more omega hydroxy acids, one or more alcohols, aldehydes, acids, esters, alkanes, alkenes, alkynes, aromatic compounds, polypeptides, peptides, lipids, sugars, carbohydrates, and/or polynucleic acid molecules may be present in the mixture. In some embodiments, organic matter such as cells and/or cellular debris may be present in the mixture.

The terms "purified", "purifying", "pure", "substantially pure" or "substantially purified" as used herein refer to a solution, solid or semi-solid mass comprising a polycarboxylic acid of interest, which solution, or solid or semi-solid mass is obtained from a starting mixture comprising the polycarboxylic acid of interest, and wherein the solution or solid or semi-solid mass comprising the polycarboxylic acid of interest is at least 5 percent more pure and up to 95 percent or more pure on a weight to weight basis (as for example comparing the weight of total solids in a starting mixture and in a mixture that has been partially or fully purified), a weight to volume basis (e.g., g/L) or on a volume to volume basis as compared with the original starting mixture containing the polycarboxylic acid of interest. In some embodiments, the purified polycarboxylic acid may be 5.1-6 percent, 6.1-7 percent, 7.1-8 percent, 8.1-9 percent, 9.1-10 percent, 10.1-11 percent, 11.1-12 percent, 12.1-13 percent, 13.1-14 percent, 14.1-15 percent, 15.1-16 percent, 16.1-17 percent, 18 percent, 19 percent, 20 percent, 21 percent, 22 percent, 23 percent, 24 percent 25 percent, 26 percent, 27 percent, 28 percent, 29 percent, 30 percent, 31-34 percent, 35 percent, 36-39 percent, 40 percent, 41-44 percent, 45 percent, 46-49 percent, 50 percent, 55 percent, 60 percent, 65 percent, 70 percent, 75 percent, 80 percent, 85 percent, 90 percent, 95 percent or greater than 95 percent more pure than the starting mixture.

The term "isolated" as used herein refers to a mixture comprising one or more polycarboxylic acids wherein the polycarboxylic acid is at least 50 percent more pure on a weight to weight basis, a weight to volume basis (eg., g/L) or on a volume to volume basis as compared with the original starting mixture containing the polycarboxylic acid of interest.

The term "organic solvent" as used herein refers to a partially aqueous liquid or a non-aqueous liquid, or to a combination of two or more non-aqueous liquids that are at least partially miscible with an aqueous liquid and have 2 to 30 or more carbons. The organic solvents particularly useful herein are those in which a polycarboxylic acid of interest in soluble at a concentration of at least ten grams per liter at seventy degrees Celsius, and wherein the organic solvent is miscible with water. Non-limiting examples of organic solvents include polar and non-polar, protic and aprotic. Selection of a suitable organic solvent or solvents for use herein is generally a function of the molecular characteristics of the polycarboxylic acid of interest to be purified such as the number of carbons, the number and location of the carboxyl groups, the presence or absence of unsaturation, the presence or absence of additional functional groups, and the like. A non-limiting example of an organic solvent suitable for use herein includes glacial acetic acid.

An organic solvent that does not react with the polycarboxylic acid of interest or with an acid may be utilized; such organic solvents include for example, methane, ethane, pentane, hexane, octane, decane, dodecane, undecane, as well as methene, ethene, butene, pentene, hexene, octene, decene, dodecene, undecene and the like. Alkynes such as hexyne, octyne, decyne and the like also can be utilized. Also useful for some embodiments are glacial acetic acid, polyethylene glycol and other glycols. In certain embodiments, aromatic compounds, and linear branched compounds may be useful.

In some embodiments, the Hansen solubility parameter model may be used to determine which organic solvent(s) are best suited for use in purifying a polycarboxylic acid of interest.

For the 12 carbon, alpha omega polycarboxylic acid known as dodecanedioic acid ("DDDA") and for other polycarboxylic acids of interest similar to DDDA, the following list of organic solvents may be useful in the purification process:

Acetic Acid (glacial), n-Butanol, sec-butanol, isobutanol, tert-butanol, 1-pentanol, 2-pentanol, 3-pentanol, 1-hexanol, 2-hexanol, 3-hexanol, 1-septanol, 1-octanol, butanone, 3-pentanone, acetone and ethyl acetate. In some embodiments, the following list of organic solvents may also be useful:

| IUPAC NAME | COMMON NAME |
|---|---|
| 2-methyloxirane | Propylene oxide |
| | Butylamine, sec- |
| 2-methylpropan-1-amine | Isobutylamine |
| butan-2-one oxime | Methyl ethyl ketoxime |
| | Butylamine, tert- |
| propan-2-yl acetate | Acetic acid, isopropyl ester |
| | Eastman isopropyl acetate |
| | Hydrazine |
| 2,2,3,3,3-pentafluoropropan-1-ol | Pentafluoropropyl alcohol |
| N-prop-2-enylprop-2-en-1-amine | Diallylamine |
| | Methyl pivalate |
| 2-butoxyethyl acetate | Butyl cellosolve acetate |
| butane-2,3-dione | Diacetyl |
| | Eastman EB acetate |
| 2-butoxyethyl acetate | Ethylene glycol monobutyl ether acetate |
| | Glycol ether EBA |
| 4-methylpentan-2-yl acetate | Methyl amyl acetate |
| Propanal | Propionaldehyde |
| Acetone | Acetone |
| 3-methylbutyl acetate | Isoamyl acetate |
| 6-acetyloxyhexyl acetate | Hexylene glycol diacetate |
| propan-2-yl formate | Isopropyl formate |
| prop-2-enyl 2-methylprop-2-enoate | Allyl methacrylate |
| butan-2-yl acetate | Acetic acid, sec-butyl ester |
| | Eastman methyl acetate |
| | Eastman n-propyl acetate |
| methyl acetate | Methyl acetate |
| propyl acetate | Propyl acetate, n- |
| methyl propanoate | Methyl propionate |
| 1,1,1-trimethoxyethane | Trimethyl orthoacetate |
| Ethanal | Acetaldehyde |
| 3-methoxybutyl acetate | Methoxybutyl acetate |
| Trimethoxymethane | Trimethyl orthoformate |
| ethyl formate | Ethyl formate |
| Dimethoxymethane | Dimethoxymethane |
| 3-methoxypropan-1-amine | Methoxypropylamine, 3- |
| | Arcosolv PNB |
| | Dowanol PnB |
| | PNB |
| 1-butoxypropan-1-ol | Propylene glycol monobutyl ether |
| | Solvenon PnB |
| methyl prop-2-enoate | Methyl acrylate |
| 1-(2-methylpropoxy)propan-2-ol | Propylene glycol monoisobutyl ether |
| | Texanol |
| | Texanol ester alcohol |
| 2,2-dimethylpropanoic | Pivalic acid |
| pentanoic acid | Valeric acid |
| Ethanamine | Ethylamine |
| | Tetrafluoro-1-propanol, 2,2,3,3- |
| | Isooctyl alcohol (mixed isomers) |

Also included herein as optionally useful organic solvents are cyclized organic molecules such as cyclohexane, cyclohexene, cyclodecane, cyclodecene and the like. Additional organic solvents included herein are petroleum distillates such as kerosene. The organic solvents of the present technology may be added to a mixture comprising the polycarboxylic acid of interest to be purified on a volume to volume, weight to weight, volume to weight or weight to volume basis. Typically, the determination will be made on a volume to volume basis. Optionally 1 volume of mixture may be combined with 0.01, 0.05, 0.10, 0.15, 0.20, 25, 0.5, 0.75, 1, 1.5, 2, 2.5, 3, 4, 5, 6, 7, 8, 9, 10, 11, 12, 13, 14, 15, 16, 17, 18, 19, 20, 25, 30, 35, 40, 45, 50, 60, 70, 80, 90, 99, or more volumes of solvent or solvents, including any volume amount in between the foregoing numbers, and volume amounts greater than 99. In addition, fractions of these volumes (such as 9.5, 25.25, 37.75 etc.) may be employed as appropriate, based in part on the desired level of purification of the polycarboxylic acid of interest. In certain embodiments, the least amount of organic solvent feasible is utilized, thereby minimizing the environmental impact of the organic solvent. Where possible, the organic solvent can be used and re-used through successive cycles of purification as a means of reducing the environmental impact. In some embodiments, a second organic solvent can be used at the same time or after a first organic solvent is employed.

In some embodiments, the at least one organic solvent may be heated prior to and/or during use for purification of the polycarboxylic acid of interest. As used herein, "heating" an organic solvent(s) or a "heated" organic solvent(s) means that the organic solvent(s) is at a temperature that is greater than the temperature of the medium or mixture comprising the polycarboxylic acid of interest prior to adding any organic solvent to such medium comprising the polycarboxylic acid of interest. In some embodiments, the organic solvent(s) is heated 1, 2, 3, 4, 5, 6, 7, 8, 9, or 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or greater than 70 degrees above the temperature of the medium comprising the polycarboxylic acid of interest to which the organic solvent is to be added. Determination of whether to employ a heated organic solvent(s) for use herein is typically a function of the solubility of the polycarboxylic acid of interest in such organic solvent(s). For most organic solvents, the solubility of a polycarboxylic acid of interest in the organic solvent(s) is increased with increasing temperature. In some embodiments, the at least one organic solvent is heated to a temperature suitable to maximize the dissolution of the polycarboxylic acid of interest without appreciable loss of the solvent.

In some embodiments, one or more of the purification steps may be conducted under pressure that is equal to or greater than atmospheric pressure.

In certain embodiments, the pH of the mixture comprising the polycarboxylic acid of interest is decreased to a low pH before treating the polycarboxylic acid of interest with one or more organic solvents. "Low pH" as used herein means any pH that is less than the pH of a mixture prior to subjecting it to a decreasing pH. Optionally, the low pH has a value that is at least 0.5, 1.0, 1.5, 2.0 or greater than 2.0 pH units below the lowest pKa of the polycarboxylic acid of interest. A low pH often is less than 5.0 and sometimes is 4.0, 3.5, 3.0, 2.5 2.0, 1.5 or a pH in between the forgoing values. In certain embodiments, the low pH is often a pH that is less than a pKa of the polycarboxylic acid of interest, and in some embodiments, the low pH is less than the lowest pKa of the polycarboxylic acid of interest. In certain embodiments, the low pH is 0.1, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0 or even more pH units lower than the pKa1 of the polycarboxylic acid of interest.

While any acid, such as an organic acid (for example acetic acid, butyric acid, formic acid etc.) or inorganic acid (for example hydrochloric acid, sulfuric acid, nitric acid, phosphoric acid and the like) can be used to reduce the pH of a mixture comprising a polycarboxylic acid of interest, acids often utilized are those that are considered strong acids (such as sulfuric acid) and/or those do not have reactive groups that can react with the polycarboxylic acid of interest. As such, in many embodiments, inorganic acids often are utilized.

In certain embodiments herein, a "separating step" or "separating steps" is/are sometimes implemented between exposing the mixture comprising a polycarboxylic acid of interest to low pH and then to an organic solvent(s). Such a separating step(s) may optionally include one or more of: centrifugation, filtration, washing with purified water or other solution at any temperature, crystallization, distillation or decantation, and/or other methods known and commonly used in biochemical separations chemistry. A separating step sometimes includes multiple sub-steps.

Where the separating step(s) comprises filtration, one or more types of filtration may be used. Examples of useful types and systems of filtration include, without limitation, microfiltration, nanofiltration, ultrafiltration, and diafiltration. Filter systems useful herein for some embodiments include, without limitation, GEA model R transverse flow filtration system (www.geafiltration.com), the GE Osmonics GH brand ultrafiltration system or the GK brand ultrafiltration system (www.gewater.com), the Hydranautics NF 245 nanofiltration system (www.hydranautics.com), and the TriSep (www.trisep.com) XN45 nanofiltration system, the Trisep UA-60 system, the Trisep UE-10 system, or the Koch HFK 328 system (www.kochfilter.com). Selection of suitable filtration procedures and systems are typically a function of the molecular size, net charge and/or polarity of the polycarboxylic acid of interest as compared with the contaminating organic molecules, salts and the like present in a particular mixture.

Where the separating step(s) comprises one or more chromatography steps, examples of useful chromatography herein include, without limitation, ion exchange (cation and/or anion) chromatography, size exclusion chromatography, adsorption chromatography (such as polymer based [divinyl benzene], activated charcoal or diatomaceous earth), affinity chromatography, reverse phase chromatography, simulated moving bed chromatography, fast protein liquid chromatography, countercurrent chromatography, displacement chromatography, high performance chromatography, or expanded bed chromatography.

The amount of a polycarboxylic acid of interest present in a mixture, solution, or organic solvent can be determined using various methods such as high performance liquid chromatography with UV detection, gas chromatography, reverse phase liquid chromatography and the like (as described at dionex.com and phenomenex.com).

An embodiment of the present invention comprises the use of a combination of low pH and a slightly polar organic solvent such as glacial acetic acid to purify a polycarboxylic acid of interest having between about 8 and 16 carbons. In particular, dicarboxylic acids such as dodecanedioic acid, sebacic acid, suberic acid, brassylic acid, myristic diacid and palmitic acid may be purified by exposing a mixture comprising the polycarboxylic acid of interest to (i) a pH in the range of 1.0 to about 4.0 to precipitate the polycarboxylic acid out of the mixture solution; (ii) resuspending the precipitated polycarboxylic acid in a suitable organic solvent such as glacial acetic acid in a ratio of 1:1 volume of mixture to volume of organic solvent up to a ratio 1:3, 1:4, 1:5, 1:6, 1:17, 1:8, 1:9, 1:10 or even greater than 1:10 (volume to volume of mixture to solvent); (iii) heating the solution of polycarboxylic acid of interest and organic solvent; (iv) centrifuging the heated solution to remove impurities; (v) decreasing the temperature of the centrifuged solution to precipitate the polycarboxylic acid of interest away from the organic solvent; and (vi) collecting the precipitated polycarboxylic acid of interest.

In some embodiments, a separation step or an increased purification step of the polycarboxylic acid of interest can be accomplished by the use of additional rounds of crystallization of the polycarboxylic acid of interest or adding one or more evaporation steps of the polycarboxylic acid of interest/organic solvent to remove certain contaminants The polycarboxylic acid of interest may precipitate from the organic solvent in the form of crystals, which crystals can then be obtained in concentrated form by evaporation of the mixture from the crystal precipitate, by filtering the crystals out or by drying.

As described herein, crystals of the polycarboxylate of interest, and mixtures thereof may be formed by subjecting a mixture containing the polycarboxylic acid of interest to at least one organic solvent, and low pH conditions at a suitable temperature. In some embodiments, the morphology, shape and size of the crystals formed may be a function of whether the polycarboxylic acid of interest is fully protonated (such that all of the carboxyl groups are in the acid form) or whether some or all of the carboxyl groups are in the salt form. In some embodiments, the type of acid or acids and the type of organic solvent or solvents used to form the crystal precipitate can affect the crystal morphology.

In some embodiments, the polycarboxylic acid of interest may be further purified or isolated by subjecting it to one or more decantation procedures. This procedure is often effective for situations in which the polycarboxylic acid is in the precipitate and the contaminants are in a liquid phase.

In some embodiments, the polycarboxylic acid of interest may be further purified by subjecting it to distillation conditions whereby contaminants are distilled away from the polycarboxylic acid of interest. Distillation may be conducted using any known procedure such as for example steam distillation, vacuum distillation, flash evaporation and the like. The selection of distillation(s) to be used is in part a function of the physical properties of the polycarboxylic acid of interest as compared with the physical properties of the contaminants.

In some embodiments, the temperature of the mixture in each step of the purification procedure may affect the resulting degree of purification of the polycarboxylic acid of interest from that step. The degree of solubility of the polycarboxylic acid of interest is often a function of the mixture in which it resides, together with the temperature of that mixture. In some purification processes herein, the temperature can be increased and/or decreased one or more times during the purification process to aid in purifying the polycarboxylic acid of interest. In some steps of the purification, the temperature may be as high as the melting temperature of the organic solvent, up to about 200 degrees Celsius. In other steps of the purification process, the temperature may be as low as one degree Celsius, or even below zero degrees Celsius.

Provided in some embodiments are methods described herein for purifying a polycarboxylic acid of interest comprising culturing a microorganism to produces the polycarboxylic acid of interest in an aqueous medium (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; and (d) collecting the purified polycarboxylic acid. In certain aspects, the aqueous medium may be a fermentation broth. In certain aspects, the fermentation broth comprises at least one feedstock which is a non-petroleum based carbon source. In some aspects, the polycarboxylic acid is obtained without any use of a petroleum based feed stock.

In one embodiment a process for purification or isolation of a polycarboxylic acid of interest involves fermenting a microorganism that either naturally or through genetic engineering produces and secretes into the culture medium a polycarboxylic acid of interest. The microorganism is optionally a yeast such as Yarrowia sp., Candida sp., Pichia sp., Klyveromyces sp., or Saccharomyces sp., however other microorganisms such as bacteria, fungi algae and the like may also be employed. The microorganism can be cultured in a medium containing one or more suitable carbon sources) such as a mono-, di- or polysaccharide (glucose, fructose, sucrose, dextrose, and the like), an alcohol such as glycerol or an oil or fatty acid such as lauric acid, oleic acid, or a mixture of oils/fatty acids such as palm oil. Optionally, a mixture of saccharides, oils and/or fatty acids may be employed as a carbon source, and such carbon sources may be included in the culture medium at the same time or at different times during the fermentation process. In addition to a carbon source, the culture medium typically contains a nitrogen source often in the form of yeast extract or ammonium sulfate, certain vitamins such as biotin, and trace amounts of minerals including, without limitation zinc, copper, boron, iodine and/or manganese. The microorganism is added to the culture medium and fermented for a period of time at a suitable pH which is typically in the range of pH 5.5 to 7.5 or 8.0, a suitable temperature which is usually 25-50 degrees Celsius, and in the presence of suitable level of dissolved oxygen, usually with stirring, while the carbon source is converted to the polycarboxylic acid of interest. Upon completion of the fermentation, the pH of the mixture of microorganism and culture broth containing the polycarboxylic acid of interest can be decreased to 4.0 or below, and optionally to a pH value that is 2 or more pH units below the lowest pKa of the polycarboxylic acid of interest, and the mixture can be centrifuged or filtered to remove the cell mass. This often results in a significant portion of the polycarboxylic acid of interest precipitating out of solution together with the spent cell mass and other solid particles, after which the mixture can be centrifuged to concentrate the precipitate containing the bulk of the polycarboxylic acid of interest. This precipitate can then be suspended in an organic solvent, which organic solvent may optionally be heated, to re-dissolve the polycarboxylic acid of interest. The organic solvent containing mixture can then undergo a separation step such as filtration or centrifugation or both, and optionally the centrifugation and/or filtration step can be conducted at the same elevated temperature. After this separation step, the liquid phase comprising the bulk of the polycarboxylic acid of interest can be cooled to room temperature or below, in which case the polycarboxylic acid of interest will likely precipitate, and this precipitate can be resuspended and subjected to additional separation steps such as crystallization to further purify it away from other contaminants.

EXAMPLES

The examples set forth below illustrate certain embodiments and are not intended in any way to limit the invention described herein.

Example 1

The solubility of the polycarboxylic acids dodecanedioic acid ("DDDA") and sebacic acid were determined for water and a combination of acetic acid and water (80% volume to volume) at room temperature (20 to 25° C.) and at 70° C. Dodecanedioic acid and sebacic acid were obtained from Sigma-Aldrich (St. Louis, Miss., USA). Each polycarboxylic acid was added to the water or acetic acid solution while mixing and kept at the appropriate temperature until the solution became supersaturated as visually determined at least 20 minutes after addition of the polycarboxylic acid. As presented in Table 1, DDDA had a solubility of less than 1 g/L in water but a solubility of over 100 g/L at 70° C. in the acetic acid solution. Sebacic acid also had a solubility of over 100 g/L at 70° C. in the acetic acid solution but less than 3 g/L at 70° C. in water.

|  |  | DDDA | SEBACIC ACID |
|---|---|---|---|
| $H_2O$ | 23.0° C. | <0.03 g/L | <0.10 g/L |
|  | 70.0° C. | <0.12 g/L | <2.6 g/L |
| 80% ACETIC ACID | 20.0° C. | <0.20 g/L | <0.20 g/L |
|  | 70.0° C. | >100 g/L | >100 g/L |

Example 2

Production of DDDA by an Engineered Mircoorganism

A one milliliter frozen glycerol stock of Candida sp. strain sAA2178 (as disclosed in international patent application PCT/US2013/076664) was inoculated into a 500 ml baffled flask containing about 80 ml of SP92 culture medium (recipe below) under sterile conditions and the flask was capped with a foam plug and placed on a shaker at 30° C. and 250 rpms for about 24 hours. This culture was used to inoculate three 500 ml baffled flask containing about 80 ml of SP92 culture medium to a starting optical density at 600 nm of 0.4 and incubated at 24 hours at about 30° C. and 250 rpm. Each culture was then used to inoculate 1.5 Liters of SP92 (75 g/L dextrose) to an initial optical density of 600 nm of 2 in a 2.5 L baffled flask and incubated for 24 hrs at about 30° C. and 250 rpms.

These cultures were used to inoculate about 200 ml of 1.5×KA1 media containing about 40.5 g/L of dextrose in a 300 L working volume stir tank fermenter. The fermenter was kept at about 35 degrees Celsius, agitation was kept at about 400 rpm, the airflow was about 1 VVM and the pH was set at about 5.8 using NaOH as base. Once dextrose was depleted the pH was increased to 6.0, glucose and ethyllaurate were each fed into the fermenter at about 1.35 g/L-h and 1.125 g/L-h respectively for the duration of the fermentation for the first twenty four hours. The feed of ethyl-laurate was increased to about 1.92 g/L and was run for an additional 110 hrs. The resulting broth had a concentration of dodecanedioic acid of about 135 g/L as determined by GC analysis.

SP92 Culture Medium (Per Liter)
Material

| YNB w/o amino acids | 6.7 g |
|---|---|
| Yeast Extract | 3.0 g |
| Ammonium Sulfate | 3.0 g |
| Potassium Phosphate, Monobasic | 1.0 g |
| Potassium Phosphate, Dibasic | 1.0 g |
| Antifoam | 0.060 g |

DeKA-2 Culture Medium (Per Liter)

| Ammonium Sulfate | 10.5 g |
| --- | --- |
| Potassium Phosphate, Monobasic | 7.65 g |
| Magnesium Sulfate | 1.54 g |
| Calcium Sulfate Dihydrate | 0.248 g |
| Citric Acid Anhydrous | 0.09 g |
| Iron (II) Sulfate | 0.06 g |
| Glucose | 40.5 g |
| Biotin, 1000x | 0.3 ml |
| Trace elements, 100x (see below) | 1.5 ml |
| Deionized Water | to 1 liter |

Trace Elements

| Boric Acid | 0.900 g |
| --- | --- |
| Cupric Sulfate | 0.110 g |
| Potassium Iodide | 0.180 g |
| Manganese Sulfate Monohydrate | 0.806 g |
| Sodium Molybdate | 0.360 g |
| Zinc Sulfate | 0.720 g |
| Deionized Water | to 1 liter |

Example 3

Purification of DDDA from Fermentation Broth

About 7800 g of the fermentation broth (containing about 13.5 DDDA by weight) was acidified to a final pH of less than 2.5 at 30° C. by adding undiluted sulfuric acid dropwise into the broth while stirring. The broth was then centrifuged at 3300 g for about 10 minutes and the supernatant was discarded. The pellet was resuspended into about 7900 g of glacial acetic acid and kept at 75° C. for an hour, and the mixture was then centrifuged at about 3300 g for about five minutes. After centrifugation, the supernatant (which contained the majority of the DDDA) was collected and the pellet was discarded. The acetic acid solution was then slowly cooled to 30° C. overnight. The resulting crystals of DDDA were collected in a Buchner funnel, and washed 4 times with 8 liters of water each time. About 853 g of DDDA were obtained from the final wash and this DDDA had a purity of about 92% (w/w). This step resulted in an approximately seven fold purification of DDDA as compared with the starting fermentation broth mixture.

Example 4

Esterification of Stearic Acid

Commercially available stearic ac vas mixed with ethanol at a 1:3 molar ratio, and 1 mol % H2SO4 was added as a catalyst. The ethanol mixture used contained 5% methanol as denaturant. The mixture was heated at 70° C. with agitation for 5 hours and the temperature was then decreased to 55° C. with agitation for 8 hours. Agitation was then halted to allow the separation of the aqueous and ethyl stearate layers. GC analysis of the ethyl stearate layer revealed a fatty acid content of 94%, 86% of which was either in the methyl or ethyl ester form.

| Component | Percentage by mass |
| --- | --- |
| Ethyl Stearate | 74 |
| Methyl Stearate | 8 |
| Stearic Acid | 11 |
| Ethanol | 1 |
| Palmitic Acid | 1 |
| Unknown | 5 |

Example 5

Production of Octadecanedioic Acid ("ODDA") by an Engineered Microorganism

A one milliliter frozen glycerol stock of *Candida* sp. yeast strain sAA2178 (disclosed in international patent application PCT/US2013/076664) was inoculated into a 500 ml baffled flask containing about 80 ml of SP92 culture medium (described in Example 2 above) under sterile conditions, and the flask was capped with a foam plug and placed on a shaker at 30° C. and 250 rpms for about 24 hours. This culture was used to inoculate three 500 ml baffled flasks containing about 80 ml of SP92 culture medium at a starting optical density of 600 nm of 0.4. The flasks were incubated at 24 hours at about 30° C. and 250 rpm after which the three flasks were combined. This combined culture was divided into three aliquots which were used to inoculate three containing 2.5 L baffled flasks containing SP92 (75 g/L dextrose) and having initial optical density of 600 nm of 2; these flasks were incubated for about 24 hrs at about 30° C. and 250 rpms.

These cultures were used to inoculate about 200 L of 1.5×KA media (described in Example 2) containing about 40.5 g/L of dextrose in a 300 L working volume stir tank fermenter. The fermenter was kept at about 34 degrees Celsius, agitation was kept at about 400 rpm, the airflow was about 1 VVM and the pH was set at about 5.8 using NaOH as base. Once dextrose was depleted the pH was increased to 6.0, glucose and ethyl-stearate mixture (74% ethyl-stearate, 18% stearic acid, 8% methyl stearate) were each fed into the fermenter at about 1.35 g/L-h and 0.9 g/L-h respectively for the duration of the 100 hour fermentation, however from hour 40 through hour 48, the rate of ethyl stearate mixture was increased to 1.8 g/L hr. The resulting broth had a concentration of dodecanedioic acid of about 40 g/L as determined by GC analysis.

Example 6

Purification of ODDA from the Fermentation Broth

About 1.51 kg of 30% $H_2SO_4$ and 2.12 kg of 98% $H_2SO_4$ was added to 274.6 kg of broth obtained from the previous Example and the pH was adjusted to about 2.56. The resulting broth was subjected to tangential flow filtration with a 0.1 micron stainless steel Graver membrane until the solids were concentrated to about 152.1 kg. The resulting broth was then further dewatered by dead-end filtration through four 1 micron polypropylene felt bags (Filter source, Hampsburg, Pa.) until full. The solids were then partially dried by passing air through the bag and then finally dried in a vacuum oven (100-150 mbar 170 Celsius) until the water content was less than 0.5% as measured by the Karl Fisher method (astm.org/standards/E203.htm) These dry solids were mixed with glacial acetic acid at a ratio of 1 kg solids/7 kg acetic acid, and the mixture was heated to 70° C.

and held at this temperature with mixing for 30 minutes. Cellular debris was removed by filtration using a 200 micron flit Buchner Funnel, and the ODDA/acetic acid filtrate was then returned to 70° C. for 15 minutes. The mixture was allowed to cool to room temperature overnight. The precipitated ODDA was recovered by filtration using a 4-7 micron Whatman 597 cellulose filter paper and washed twice with water to 100% of the original volume. The recovered crude ODDA was collected in trays and dried in warm vacuum ovens. The resulting material was about 69.6% octadecanedioic acid. This step resulted in an approximate seventeen fold purification of ODDA as compared with the starting fermentation broth.

Example 7

Selected Embodiments

Listed hereafter are non-limiting examples of embodiments of the present invention.

A1. A method for purifying a polycarboxylic acid of interest from an aqueous mixture, comprising: (a) reducing the pH of the aqueous medium comprising the polycarboxylic acid such that the polycarboxylic acid is precipitated from said medium; (b) contacting the precipitated polycarboxylic acid with at least one suitable organic solvent at one or more selected temperatures; (c) separating the polycarboxylic acid from the at least one suitable organic solvent; and (d) collecting the purified polycarboxylic acid.

A2. The method of any of embodiments A1 to A4, comprising a separating process between (a) and (b).

A3. The method of embodiment A1 wherein the aqueous solution is a fermentation broth.

A4. The method of any of embodiments A1-A3 wherein the polycarboxylic acid of interest is a dicarboxylic acid.

A5. The method of embodiment A4, wherein the polycarboxylic acid is chosen from azelaic acid, sebacic acid, UDDA, DDDA, brassylic acid, TDDA, thapsic acid, traumatic acid, octadecanedioic acid, 9-octadecenedioic acid, octadeca-c6,c9-diene-1,18-dioate octadeca-c3,c6,c9-triene-1,18-dioate, and icosanedioic acid.

A6. The method of embodiment A5 wherein the polycarboxylic acid is DDDA.

A7. The method of any one of embodiments A1 to A6, wherein the organic solvent is an acid.

A8. The method of embodiment A7 wherein the organic solvent is acetic acid.

A9. The method of embodiment A8 wherein the organic solvent is heated to solubilize the polycarboxylic acid of interest.

A10. The method of embodiment A9 wherein the organic solvent is slowly cooled after heating thereby precipitating the polycarboxylic acid of interest.

A11. The method of embodiment A10 wherein the polycarboxylic acid is DDDA, the organic solvent is acetic acid is heated to about 70 degrees Celsius and then cooled to about 25 degrees Celsius.

A12. The method of any of embodiments A1-A11 further comprising one or more separating steps.

A13. The method of any of embodiments A1-A12 wherein the polycarboxylic acid is at least 5 percent more pure on a weight to weight basis as compared with the starting mixture.

B1. A composition comprising a polycarboxylic acid of interest, wherein the polycarboxylic acid of interest is made according to the method of embodiment A1.

B2. The composition of embodiment B1 wherein the polycarboxylic acid of interest is DDDA.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for purifying a polycarboxylic acid of interest from an aqueous mixture, comprising: (a) contacting the aqueous mixture comprising the polycarboxylic acid with at least one acid such that the polycarboxylic acid is precipitated from said aqueous mixture; (b) contacting the precipitated polycarboxylic acid with at least one organic solvent at one or more selected temperatures; (c) separating the polycarboxylic acid from the at least one organic solvent; and (d) collecting the purified polycarboxylic acid.

2. The method of claim 1, wherein the aqueous mixture is a fermentation broth.

3. The method of claim 2, wherein the polycarboxylic acid of interest is a dicarboxylic acid.

4. The method of any one of claims 1-3, comprising a separating process between (a) and (b).

5. The method of claim 4, wherein the polycarboxylic acid is chosen from the group consisting of azelaic acid, sebacic acid, UDDA, DDDA, brassylic acid, TDDA, thapsic acid, traumatic acid, octadecanedioic acid, 9-octadecenedioic acid, octadeca-c6,c9-diene-1,18-dioate octadeca-c3,c6,c9-triene-1,18-dioate, and icosanedioic acid.

6. The method of claim 5, wherein the polycarboxylic acid is DDDA.

7. The method of any one of claims 1-6, wherein the organic solvent is an acid.

8. The method of claim 7, wherein the organic solvent is acetic acid.

9. The method of any one of claims 1-8, wherein the organic solvent is heated to solubilize the polycarboxylic acid of interest.

10. The method of claim 9, wherein the organic solvent is slowly cooled after heating thereby precipitating the polycarboxylic acid of interest.

11. The method of claim 10, wherein the polycarboxylic acid is DDDA, and the organic solvent is acetic acid which is heated to about 70 degrees Celsius and then cooled to about 25 degrees Celsius.

12. The method of any of claims 1-11, further comprising one or more separating steps.

13. The method of any of claims 1-12, wherein the purified polycarboxylic acid is at least 5 percent more pure on a weight to weight basis as compared to the polycarboxylic acid in the starting mixture.

14. A composition comprising a polycarboxylic acid of interest purified according to the method of any one of claims 1-13.

15. The composition of claim 14, wherein the polycarboxylic acid of interest is DDDA.

* * * * *